United States Patent
Xu et al.

(10) Patent No.: US 12,318,385 B2
(45) Date of Patent: Jun. 3, 2025

(54) PHARMACEUTICAL COMPOSITION COMPRISING PARP INHIBITORS

(71) Applicant: Jiangsu Hengrui Medicine CO., LTD., Jiangsu (CN)

(72) Inventors: Jiajia Xu, Jiangsu (CN); Hao Chen, Jiangsu (CN); Xu Wang, Jiangsu (CN)

(73) Assignee: Jiangsu Hengrui Medicine CO., LTD., Jiangsu (CN)

( * ) Notice: Subject to any disclaimer, the term of this patent is extended or adjusted under 35 U.S.C. 154(b) by 795 days.

(21) Appl. No.: 17/292,846

(22) PCT Filed: Nov. 15, 2019

(86) PCT No.: PCT/CN2019/118714
§ 371 (c)(1),
(2) Date: May 11, 2021

(87) PCT Pub. No.: WO2020/098774
PCT Pub. Date: May 22, 2020

(65) Prior Publication Data
US 2021/0393626 A1   Dec. 23, 2021

(30) Foreign Application Priority Data
Nov. 16, 2018   (CN) .......................... 201811363490.6

(51) Int. Cl.
*A61K 31/502*  (2006.01)
*A61K 9/48*    (2006.01)

(52) U.S. Cl.
CPC ............ *A61K 31/502* (2013.01); *A61K 9/485* (2013.01); *A61K 9/4858* (2013.01); *A61K 9/4866* (2013.01)

(58) Field of Classification Search
CPC .... A61K 31/502; A61K 9/485; A61K 9/4858; A61K 9/4866
See application file for complete search history.

(56) References Cited

U.S. PATENT DOCUMENTS

| | | | |
|---|---|---|---|
| 9,089,546 B2 * | 7/2015 | Chen | A61K 31/352 |
| 9,273,052 B2 * | 3/2016 | Tang | A61K 45/00 |
| 2012/0039995 A1 * | 2/2012 | Gu | A61P 35/02 |
| | | | 556/77 |

FOREIGN PATENT DOCUMENTS

| | | | |
|---|---|---|---|
| CN | 102372716 A | 3/2012 | |
| CN | 104434809 A | 3/2015 | |
| EP | 3299014 A1 * | 3/2018 | ........... A61K 31/502 |
| JP | 2013-537530 A | 10/2013 | |
| JP | 2018-507896 A | 3/2018 | |

OTHER PUBLICATIONS

Feb. 21, 2020 (WO)—International Search Report PCT/CN2019/118714.
D'Amours et al. "Poly(ADP-ribosyl)ation reactions in the regulation of nuclear functions". Biochem. J. (1999) 342, 249-268.
Plummer. "Inhibition of poly(ADP-ribose) polymerase in cancer". Current Opinion in Pharmacology 2006, 6:364-368.
Ratnam et al. "Current Development of Clinical Inhibitors of Poly(ADP-Ribose) Polymerase in Oncology". Clin Cancer Res 2007;13:1383-1388. Published online Mar. 1, 2007.

* cited by examiner

*Primary Examiner* — Joseph K McKane
*Assistant Examiner* — Quincy McKoy
(74) *Attorney, Agent, or Firm* — Banner & Witcoff, Ltd.

(57) ABSTRACT

A solid dispersion for PARP inhibitors, comprising a compound represented by formula I and a carrier material, wherein the carrier material comprises polyvinylpyrrolidone. A pharmaceutical composition, comprising a solid dispersion, a filler, a disintegrating agent and a lubricant. A preparation method for the solid dispersion. Use of the solid dispersion or the pharmaceutical composition in the preparation of drugs for treating cancers.

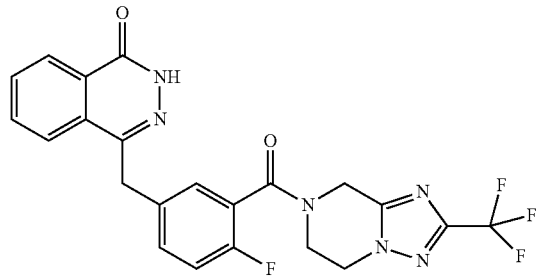

I

16 Claims, 1 Drawing Sheet

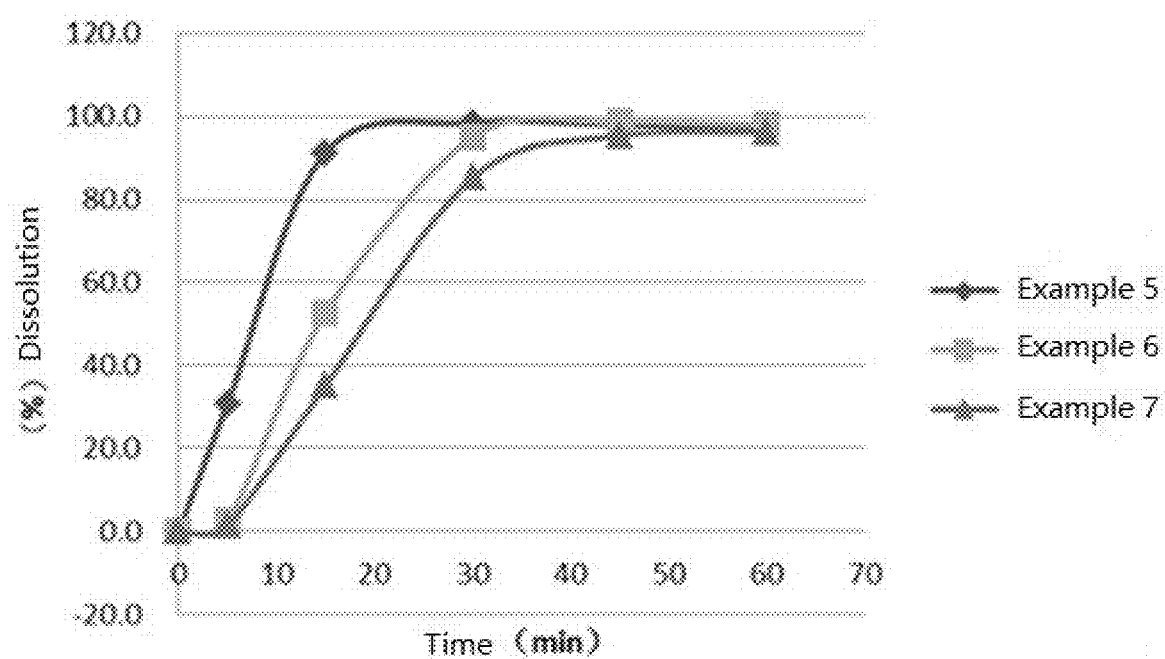

PHARMACEUTICAL COMPOSITION COMPRISING PARP INHIBITORS

RELATED APPLICATION DATA

This application is a National Stage Application under 35 U.S.C. 371 of co-pending PCT application number PCT/CN2019/118714 filed on Nov. 15, 2019; which claims the benefit of Chinese Patent Application number CN201811363490.6 filed on Nov. 16, 2018, each of which are hereby incorporated by reference in their entireties.

TECHNICAL FIELD

The present disclosure belongs to the field of pharmaceutical formulations, in particular relates to a pharmaceutical composition comprising PARP inhibitors and a preparation method thereof.

BACKGROUND

Poly (ADP-ribose) polymerases (PARPs) characterized by polyadenosine diphosphate-ribosylation activity constitute a superfamily comprising 18 nuclear and cytoplasmic enzymes. This polyadenosine diphosphate-ribosylation modulates the catalytic activity of a target protein and interactions between proteins, and regulates many basic biological processes, including DNA repair, cell death, as well as genomic stability (see D'Amours et al. Biochem. J, 1999, 342, 249).

PARP-1 activity accounts for approximately 80% of the total cellular PARP activity, and becomes a member of the PARP family capable of repairing DNA damages together with PARP-2 which is the most similar to PARP-1. As a DNA damage sensor and signaling protein, PARP-1 can rapidly detect and bind directly to DNA damage sites, and then induce aggregation of a variety of proteins required for DNA repair, thereby enabling DNA damage to be repaired. When PARP-1 is deficient in cells, PARP-2 can replace PARP-1 for repairing DNA damages.

Studies demonstrate that PARPs protein expression is generally enhanced in solid tumors compared with normal cells. In addition, tumors (breast tumors and ovarian cancer) with deletions in DNA repair-related genes such as BRCA-1 or BRCA-2 demonstrate extreme sensitivity to a PARP-1 inhibitor, suggesting a potential use of PARP inhibitors as a single agent in the treatment of this so-called triple-negative breast cancer. (See Plummer, E. R. Curr. Opin. Pharmacol. 2006, 6, 364; Ratnam, et al; Clin. Cancer Res. 2007, 13, 1383). At the same time, PARP-1 is considered as an effective target for exploring new cancer therapies, since the DNA damage repair mechanism is the main mechanism by which tumor cells develop tolerance to chemotherapeutic agents and an ionizing radiation therapy.

CN102372698A discloses a novel phthalazinone derivative (Formula I) that exhibits strong inhibition and adjuvant cancer therapy of poly(ADP-ribose) polymerases (PARPs), as shown below:

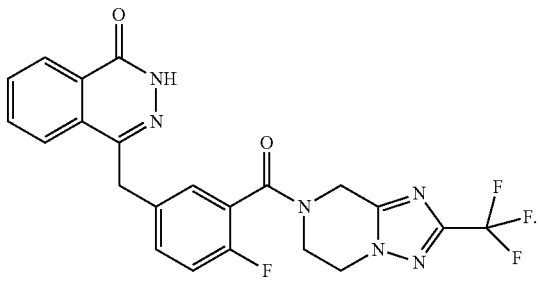

The prior art reports some compositions comprising PARP inhibitors and a preparation method thereof. CN102238945A describes pharmaceutical compositions comprising a solid dispersion of olaparib, wherein the carrier material for the solid dispersion is copovidone, and indicates that the solid dispersion has poor stability when PVP is used as a carrier material.

CONTENT OF THE PRESENT DISCLOSURE

The purpose of the present disclosure is to provide a solid dispersion comprising a compound represented by formula I and a pharmaceutical composition for improvement of the treatment effect of drugs.

One aspect of the present disclosure provides a solid dispersion, comprising a compound represented by formula I and a carrier material, wherein the carrier material comprises polyvinylpyrrolidone.

In some embodiments, the compound represented by formula I is in an amorphous form.

The weight ratio of the compound represented by formula I to the polyvinylpyrrolidone may be 1:0.1 to 1:10, preferably 1:0.1 to 1:7, more preferably 1:0.5 to 1:5, and the most preferably 1:3.

The polyvinylpyrrolidone may be of the type of polyvinylpyrrolidone frequently used in the formulation, which may be classified based on K values, such as PVPK12, PVPK15, PVPK17, PVPK25, PVPK30, PVPK60, and PVPK90, or based on cross-linked polymers with molecular weights ranging from 2,500 to 1,200,000.

In some embodiments, the solid dispersion may further comprise other carrier materials, wherein the proportion of polyvinylpyrrolidone may be greater than 40%, 50%, 60%, 70% or more based on the total weight of the solid dispersion.

In some embodiments, the solid dispersion consists of a compound represented by formula I and a carrier material polyvinylpyrrolidone.

The solid dispersion may be further used to prepare a pharmaceutical composition comprising the compound represented by formula I, such as an oral formulation, an injection, an inhalation formulation, or a topical formulation, such as tablets, capsules, injections, lyophilized powder for injection, etc.

The pharmaceutical composition of the present disclosure may be an oral formulation, an injection, an inhalation formulation, or a topical formulation, such as tablets, capsules, injections, and lyophilized powder for injection.

The solid dispersion of the present disclosure may be prepared by methods well known in the art, such as methods of melt extrusion, spray drying, solvent evaporation, etc.

For example, the method comprises a step of mixing the compound represented by formula I with the polyvinylpyrrolidone and an optional excipient in a melt extrusion device, and a step of heating and mixing the mixture and finally extruding a solid dispersion product. The mixture is heated by an extruder to a temperature high enough to melt the mixture but low enough to not degrade active components.

Alternatively, the method comprises a step of mixing the compound represented by formula I with the polyvinylpyrrolidone and a solvent, and a step of removing the solvent. The solid dispersion may be prepared by mixing with an additional excipient as required. Methods for solvent removal may be rotary evaporation, spray drying, lyophilization, film evaporation, etc. The solvent may be a ketone solvent and an alcohol solvent, wherein the ketone solvent is preferably acetone, and the alcohol solvent is preferably ethanol.

Another aspect of the present disclosure provides a pharmaceutical composition comprising a solid dispersion comprising the compound represented by formula I, and one or more pharmaceutically acceptable excipients.

In some embodiments, the content of the compound represented by formula I is 0.01%-50%, preferably 1%-40% (such as 4%, 22%) based on the total weight of the pharmaceutical composition.

In some embodiments, the content of the compound represented by formula I is 0.1 mg-1000 mg, e.g. 1 mg-500 mg, e.g. 5 mg-200 mg, e.g. 10 mg, 40 mg, 100 mg.

In some embodiments, the pharmaceutical composition comprises a filler. One of the pharmaceutically acceptable excipients of the pharmaceutical composition may be the filler. The filler of the present disclosure may include, but are not limited to, one or more of microcrystalline cellulose, calcium hydrogen phosphate, mannitol, pregelatinized starch, lactose, preferably lactose. The content of the filler may be 5%-90% (e.g. 81%) based on the total weight of the pharmaceutical composition.

In some embodiments, the pharmaceutical composition comprises a disintegrating agent. One of the pharmaceutically acceptable excipients of the pharmaceutical composition may be the disintegrating agent. The disintegrating agent may include, but is not limited to, one or more of croscarmellose sodium, starch, sodium carboxymethyl starch, and crospovidone, preferably the sodium carboxymethyl starch. The disintegrating agent content may be 1%-20% (e.g. 2.2%, and 11.9%) based on the total weight of the pharmaceutical composition.

In some embodiments, the pharmaceutical composition comprises a lubricant. One of the pharmaceutically acceptable excipients of the pharmaceutical composition may be the lubricant. The lubricant may include, but are not limited to, one or more of magnesium stearate, zinc stearate, glyceryl behenate, sodium lauryl sulfate, hydrogenated vegetable oil, micronized silica gel, talc, silica, preferably one or more of the magnesium stearate and the silica. The content of the lubricant may be 0.5%-5% (e.g. 1.3%, 3%) based on the total weight of the pharmaceutical composition.

Other suitable excipients include adhesives, suspending agents, sweeteners, flavoring agents, preservatives, buffering agents, wetting agents, effervescent agents, etc. These excipients are well known in the art.

Another aspect of the present disclosure provides a pharmaceutical composition comprising:

| Solid Dispersion | Compound represented by formula I | 1%-40% |
|---|---|---|
| | Polyvinylpyrrolidone | 1%-85% |
| | Filler | 0%-90% |
| | disintegrating agent | 1%-20% |
| | Lubricant | 0.5-5% | based on the total weight of the pharmaceutical composition; wherein the filler is selected from one or more of microcrystalline cellulose, calcium hydrogen phosphate, mannitol, pregelatinized starch, and lactose, preferably lactose; the disintegrating agent is selected from one or more of croscarmellose sodium, starch, sodium carboxymethyl starch and crospovidone, preferably sodium carboxymethyl starch; the lubricant is selected from one or more of magnesium stearate, zinc stearate, glyceryl behenate, sodium lauryl sulfate, hydrogenated vegetable oil, micronized silica gel, talc, and silica, preferably magnesium stearate and/or silicon dioxide; when the lubricant is magnesium stearate and silicon dioxide, the mass ratio of the magnesium stearate to the silica is 10:1 to 1:1, preferably 7:1 to 2:1.

In some embodiments, the content of the compound represented by formula I in the pharmaceutical composition is 4%-22% based on the total weight of the pharmaceutical composition.

In some embodiments, the content of the polyvinylpyrrolidone in the pharmaceutical composition is 12%-64% based on the total weight of the pharmaceutical composition.

In some embodiments, the content of the filler in the pharmaceutical composition is 0%-80.3% based on the total weight of the pharmaceutical composition.

In some embodiments, the content of the disintegrating agent in the pharmaceutical composition is 2.2%-11.9% based on the total weight of the pharmaceutical composition.

In some embodiments, the content of the lubricant in the pharmaceutical composition is 1.3%-3% based on the total weight of the pharmaceutical composition.

Another aspect of the present disclosure provides a pharmaceutical composition consisting of the compound represented by formula I described above, the polyvinylpyrrolidone described above, the filler described above, the disintegrating agent described above, and the lubricant described above.

Another aspect of the present disclosure provides a pharmaceutical composition comprising a compound represented by formula I, polyvinylpyrrolidone, a filler, a disintegrating agent and a lubricant, preferably comprising 1%-40% of the compound represented by formula I, 1%-85% of the polyvinylpyrrolidone, 0%-90% of the filler, 1%-20% of the disintegrating agent and 0.5%-5% of the lubricant based on the total weight of the pharmaceutical composition; preferably comprising 4% of the compound represented by formula I, 12.1% of the polyvinylpyrrolidone, 80.3% of the lactose, 2.2% of the sodium carboxymethyl starch, 0.2% of the silica and 1.2% of the magnesium stearate, or comprising 21.3% of the compound represented by formula I, 63.8% of the polyvinylpyrrolidone, 11.9% of the sodium carboxymethyl starch, 1% of the silicon dioxide and 2% of the magnesium stearate based on the total weight of the pharmaceutical composition.

Another aspect of the present disclosure provides a pharmaceutical composition comprising a compound represented by formula I, polyvinylpyrrolidone, a filler, a disintegrating agent and a lubricant, preferably comprising 1%-40% of the compound represented by formula I, 1%-85% of the polyvinylpyrrolidone, 0%-90% of the filler, 1%-20% of the disintegrating agent and 0.5%-5% of the lubricant based on the total weight of the pharmaceutical composition; preferably comprising 4% of the compound represented by formula I, 12.1% of the polyvinylpyrrolidone, 80.3% of the lactose, 2.2% of the sodium carboxymethyl starch, 0.2% of the silica and 1.2% of the magnesium stearate, or comprising 21.3% of the compound represented by formula I, 63.8% of the polyvinylpyrrolidone, 11.9% of the sodium carboxymethyl starch, 1% of the silicon dioxide and 2% of the magnesium stearate based on the total weight of the pharmaceutical composition.

Another aspect of the present disclosure provides a method for preparing the pharmaceutical composition comprising the compound represented by formula I of the present disclosure, wherein the method comprises the step of mixing the solid dispersion of the present disclosure with one or more pharmaceutically acceptable excipients.

In some embodiments, the pharmaceutical composition of the present disclosure can be prepared into an oral formulation, an injection, an inhalation formulation, or a topical formulation, such as tablets, capsules, injections, lyophilized powder for injection, etc.

In some embodiments, the pharmaceutically acceptable excipient comprises one or more of a filler, a disintegrating agent, and a lubricant, wherein the types and amounts of the filler, the disintegrating agent and the lubricant are the same as previously described.

Other suitable excipients include adhesives, suspending agents, sweeteners, flavoring agents, preservatives, buffering agents, wetting agents, effervescent agents, etc. These excipients are well known in the art.

The preparation method may be common methods in the art, for example, when preparing the oral formulation, the product may be prepared as granules, e.g., in the steps of preparing the pharmaceutical composition granules by means of dry granulator granulation, high-speed shear granulation, fluidized bed one-step granulation, etc., optionally mixing with other excipients, and then tableting (coating) or filling capsules to prepare tablets, granules or capsules.

Another aspect of the present disclosure provides a pharmaceutical composition comprising a compound represented by formula I dispersed in a carrier material, and one or more pharmaceutically acceptable excipients, wherein the compound represented by formula I is in an amorphous form.

The content of the compound represented by formula I is the same as previously described. The content and the type of the carrier material are same as previously described. The content and the type of the excipient are same as previously described.

The method for dispersing the compound represented by formula I in a carrier material is same as the method for preparing the solid dispersion of the present disclosure.

In some embodiments, the solid dispersion of the present disclosure is held at 25° C. and 60% RH for 12 months, and the purity of the compound represented by formula I is not less than 93%, e.g., the purity may be not less than 93.5%, 94%, 94.5%, 95%, 95.5%, 96%, 96.5%, 97%, 97.5%, 98%, 98.5% or higher, preferably not less than 95%, and more preferably not less than 97%.

In some embodiments, the solid dispersion of the present disclosure is held at 40° C. and 75% RH for 6 months, and the purity of the compound represented by formula I is not less than 93%, e.g., the purity may be not less than 93.5%, 94%, 94.5%, 95%, 95.5%, 96%, 96.5%, 97%, 97.5%, 98%, 98.5% or higher, preferably not less than 95%, and more preferably not less than 97%.

In some embodiments, the pharmaceutical composition of the present disclosure is subjected to the dissolution testing according to the Dissolution Test, Method 2 (Paddle) Appendix, Volume II, Chinese Pharmacopoeia 2015 in the following steps of using 0.5% Tween aqueous solution as a dissolution medium, preferably 1000 mL, and dissolving at a paddle speed of 50 rpm at 37±0.5° C. The dissolution of the compound represented by formula I is greater than 90% within 60 minutes, preferably greater than 93%, more preferably greater than 94%, and the most preferably more than 95%.

In some embodiments, the pharmaceutical composition of the present disclosure is held at 40° C. and 75% RH for 6 months, and the purity of the compound represented by formula I is not less than 93%, e.g., the purity may be not less than 93.5%, 94%, 94.5%, 95%, 95.5%, 96%, 96.5%, 97%, 97.5%, 98%, 98.5% or higher, preferably not less than 95%, more preferably not less than 97%, and the most preferably not less than 98%.

Another aspect of the present disclosure provides a use of the solid dispersion or the pharmaceutical composition comprising the compound represented by formula I of the present disclosure in the preparation of drugs for treating cancers. The cancers are selected from breast cancer, ovarian cancer, pancreatic cancer, prostate cancer, liver cancer or colon cancer, etc.

The present disclosure prepares a solid dispersion by using polyvinylpyrrolidone as a carrier, and the finally obtained pharmaceutical composition has good dissolution characteristics. In addition, the stability and the dissolution of the composition can be well maintained after a long time of storage.

BRIEF DESCRIPTION OF THE DRAWINGS

FIG. 1 is dissolution profiles of the capsules of Examples 5-7.

DETAILED DESCRIPTION OF THE EMBODIMENT

Example 1

Referring to tests under the General Notices, Volume II, Chinese Pharmacopoeia 2010, excessive compounds represented by formula I which were grinded to fine powder were weighed and transferred in a certain amount of solvent (25° C.±2° C.), and shaken vigorously for 30 s every 5 min. The dissolution of the drug was observed within 30 min. Then the solution was filtered, the initial filtrate was discarded, and the concentration of the successive filtrate was tested. The solubility was calculated.

TABLE 1

Dissolution of Compound represented by formula I in Different Solvents

| Solvent | 0.1 mol/L Hydrochloric Acid | Acetate Buffer pH 4.5 | Phosphate Buffer pH 6.8 | Purified Water | 5% Polysorbate 80 Aqueous Solution | Tetrahydrofuran | Acetone | Anhydrous Ethanol |
|---|---|---|---|---|---|---|---|---|
| Volume of Solvent/mL | 50 | 50 | 50 | 50 | 20 | 20 | 20 | 20 |
| Weight of Sample/mg | 50 | 50 | 50 | 50 | 400 | 400 | 400 | 400 |
| Approximate Solubility/µg/mL | 0.78 | 0.85 | 0.59 | Not detected | 19.5 | 8548.8 | 4958.3 | 458.2 |
| Solubility | Practically insoluble | Practically insoluble | Practically insoluble | Practically insoluble | Practically insoluble | Slightly soluble | Slightly soluble | Very slightly soluble |

As shown in test results, the compound represented by formula I was slightly soluble in the acetone and the tetrahydrofuran, very slightly soluble in the absolute ethanol, and practically insoluble in conventional aqueous solvents, and the solubilizing effect of a surfactant on the raw material was limited, so it is not possible to prepare formulations by conventional means.

Examples 2-3

TABLE 2

Components of Solid Dispersion

| | Ingredients | Example 2 | Example 3 |
|---|---|---|---|
| Solid Dispersion | Compound represented by formula I | 5.00 g | 5.00 g |
| | PVP K30 | 15.00 g | — |
| | Copovidone S630 | — | 15.00 g |
| | Acetone* | 500.00 mL | 500.00 mL |
| | Ethanol* | 30.00 mL | 30.00 mL |

Note:
*Solvents are removed during the production process.

The prescribed amount of copovidone S630 or PVPK30 was added and dissolved in ethanol. The prescribed amount of acetone was added, stirred and mixed well. The compound represented by formula I was added to the solution described above. The solution was heated to 60° C. and stirred until the compound represented by formula I was completely dissolved. After the solution was spray-dried, the obtained powder was dried at 60° C. to obtain a solid dispersion.

Example 4

The physical stability of the two solid dispersions in Examples 2 and 3 under high temperature (40° C. and 60° C.) and humidity (25° C., RH 75±5%, 25° C., RH 90±5%) as well as the chemical stability under accelerated conditions were investigated, respectively. The appearance and changes in crystal forms of the two solid dispersions in a watch glass were compared. In addition, residual solvents of the two solid dispersions were tested.

Test method of the residual solvents: A gas chromatography, a DB-5 capillary column (30 m×0.53 mm×1.0 µm) and a flame ionization detector (FID) were used, with water as a solvent.

Test methods for the content of active substances and total impurities (same below): A high performance liquid chromatography system was used for testing, with Phenomenex Luna C18 column (4.6 mm×200 mm, 5 µm), mobile phase: 0.02 mol/L potassium dihydrogen phosphate solution/acetonitrile, and detection wavelengths: 254 nm, and 200 nm.

TABLE 3

Stress Test

| Storage Conditions | Time | Example 2 Description | Example 2 Crystal Form | Example 3 Description | Example 3 Crystal Form |
|---|---|---|---|---|---|
| 60° C. | 5 d | White Powder | Amorphous | White Powder | Amorphous |
| | 10 d | White Powder | Amorphous | White Powder | Amorphous |
| | 30 d | White Powder | Amorphous | White Powder | Amorphous |
| 40° C. | 5 d | White Powder | Amorphous | White Powder | Amorphous |
| | 10 d | White Powder | Amorphous | White Powder | Amorphous |
| | 30 d | White Powder | Amorphous | White Powder | Amorphous |
| 25° C., RH90 ± 5% | 5 d | White Powder | Amorphous | Deliquescent | Amorphous |
| | 10 d | White Powder | Amorphous | Deliquescent | Amorphous |
| | 30 d | White Powder | Amorphous | Viscous | Amorphous |
| 25° C., RH75 ± 5% | 5 d | White Powder | Amorphous | White Powder | Amorphous |
| | 10 d | White Powder | Amorphous | White Powder | Amorphous |
| | 30 d | White Powder | Amorphous | Clumpy | Amorphous |

TABLE 4

Test for Residual Solvents of Solid Dispersions

|  |  | Example 2 | Example 3 |
|---|---|---|---|
| Residual Solvent/ppm | Butanone | Not detected | Not detected |
|  | Acetone | 112 | 478 |
|  | Ethanol | 98 | 468 |

TABLE 5

Stability Test Data for Solid Dispersion

| Item |  |  | Example 2 | Example 3 |
|---|---|---|---|---|
| Related Substance/% | 60° C. RH 75% 0 day | Total impurities | 1.18 | 1.06 |
|  | 60° C. RH 75% 1 month | Total impurities | 1.36 | 1.44 |

The solid dispersion prepared from the copovidone was more hygroscopic than PVP, and was deliquescent after 5 days and viscous after 30 days at RH90±5%, while the solid dispersion prepared by the PVP was more stable in appearance. In addition, the solid dispersion prepared from PVP had fewer residual solvents. After one month under accelerated conditions, the impurity content of the solid dispersion prepared from PVP increased less and the impurity content of the solid dispersion prepared from copovidone increased more.

Examples 5-7

TABLE 6

Raw Materials of Capsules of Different Strengths

|  |  | Example 5 | Example 6 | Example 7 |
|---|---|---|---|---|
|  | Strengths | 10 mg | 40 mg | 100 mg |
| Raw | Solid Dispersion | 40 mg | 160 mg | 400 mg |
| Materials | Lactose | 200 mg | — | — |
|  | Sodium Carboxymethyl Starch | 5.58 mg | 22.32 mg | 55.8 mg |
|  | Silicon Dioxide | 0.46 mg | 1.86 mg | 4.65 mg |
|  | Magnesium Stearate | 2.92 mg | 3.72 mg | 9.3 mg |
|  | Total | 248.96 mg | 187.90 mg | 469.75 mg |

The solid dispersion of the compound represented by formula I of Example 2, the lactose (Example 5), the sodium carboxymethyl starch, the silica, and a portion of the magnesium stearate were mixed well. The mixture was put in a dry granulator for dry granulation, mixed well with the remaining magnesium stearate after granulation, and filled in capsules to prepare capsules.

Example 8

The dissolution of capsules of Examples 5-7 was tested according to the Dissolution Test, Method 2 (Paddle) Appendix, Volume II, Chinese Pharmacopoeia 2015. The dissolution test for capsules of Examples 5, 6 and 7 was performed at a paddle speed of 50 rpm at 37±0.5° C. using 1000 mL of 0.5% Tween aqueous solution as a dissolution medium, respectively. Dissolution profiles are shown in FIG. 1. The dissolution results showed that all capsules of different strengths can be dissolved rapidly and completely.

Example 9

Samples of Example 2 were stored for 12 months under long-term conditions (25° C./60% relative humidity) and 6 months under accelerated conditions (4° C./75% relative humidity) in a packaging material (sealed in pharmaceutical low-density polyethylene bags with a desiccant and aluminum foil pouches), and samples were periodically collected for testing the purity of active substances, impurities, apparent solubility (solubility in 0.5% polysorbate 80 aqueous solution), and crystallization. Results are shown in the following table.

TABLE 7

Stability Study of Samples in Example 2 under Different Conditions

| Conditions | Time | Content of Active Substance (%) | Total Impurities (%) | Apparent Solubility (mg/mL) | Crystallization |
|---|---|---|---|---|---|
| | Initial | 98.9 | 0.44 | 0.68 | Amorphous |
| 25° C. ± 2° C., RH60% ± 5% | March | 98.8 | 0.44 | 0.50 | Amorphous |
| | June | 98.8 | 0.47 | 0.53 | Amorphous |
| | September | 98.9 | 0.57 | 0.70 | Amorphous |
| | December | 99.3 | 0.58 | 0.66 | Amorphous |
| 40° C. ± 2° C., RH75% ± 5% | March | 98.7 | 0.46 | 0.50 | Amorphous |
| | June | 98.5 | 0.57 | 0.51 | Amorphous |

As shown in the results, the solid dispersion prepared by the PVP was stable after long-term storage, and the dissolution can also be maintained.

Example 10

Capsules of Example 7 were placed in polyvinyl chloride sheets for solid pharmaceutical use and aluminum foils for pharmaceutical packaging, after heat sealing, packaged with a composite film bag for pharmaceutical packaging, and then placed into a carton after heat sealing. Samples were periodically collected after storage at 40° C.±2° C. and RH75%±5% for 6 months, and samples were periodically collected after storage at 30° C.±2° C. and RH65%±5% for 6 months, respectively, in order to test the purity of active substances, impurities and dissolution (at 45 mm, with the dissolution test method the same as that in Example 8). Results are shown in the following table.

TABLE 8

Stability Study of Capsules in Example 7 under Different Conditions

| Test Items | 0 d | 40° C. ± 2° C., RH75% ± 5% | | | | 30° C. ± 2° C., RH65% ± 5% | |
|---|---|---|---|---|---|---|---|
| | | 1 M | 2 M | 3 M | 6 M | 3 M | 6 M |
| Appearance | White Powder | White Powder | White Powder | White Powder | White Powder | White Powder | White Powder |
| Dissolution (%) | 92 | 98 | 96 | 95 | 96 | 96 | 95 |
| Purity of Active Substance (%) | 99.6 | 99.7 | 99.6 | 99.6 | 99.7 | 99.6 | 99.6 |
| Total Impurities (%) | 0.31 | 0.30 | 0.32 | 0.33 | 0.40 | 0.29 | 0.31 |

After the samples were subject to the accelerated test and the long-term test after stored at 40° C.±2° C./RH75%±5% and 30° C.±2° C./RH65±5% for 6 months, no significant changes were observed in each parameter, and the stability was excellent.

Although the detailed embodiments of the present disclosure are described above, technicians skilled in the art should understand that the embodiments are only examples, and many changes or modifications can be made to the embodiments without departing from principles and essence of the present disclosure. Therefore, the protection scope of the present disclosure is defined by the appended claims.

What is claimed is:

1. A solid dispersion, wherein the solid dispersion consists of a compound represented by formula I and polyvinylpyrrolidone, the weight ratio of the compound represented by formula I to the polyvinylpyrrolidone is 1:3 to 1:7, and the proportion of polyvinylpyrrolidone is greater than 70% based on the total weight of the solid dispersion;

2. The solid dispersion of claim 1, wherein the compound represented by formula I is in an amorphous form.

3. The solid dispersion of claim 1, wherein the weight ratio of the compound represented by formula I to the polyvinylpyrrolidone is 1:3.

4. The solid dispersion of claim 1, wherein the polyvinylpyrrolidone is selected from PVP K12, PVP K15, PVP K17, PVP K25, PVP K30, PVP K60 and PVP K90.

5. The solid dispersion of claim 1, wherein the polyvinylpyrrolidone is PVP K30.

6. The solid dispersion of claim 1, wherein the solid dispersion is held at 25° C. and 60% RH for 12 months, and the purity of the compound represented by formula I is not less than 93%, 93.5%, 94%, 94.5%, 95%, 95.5%, 96%, 96.5%, 97%, 97.5%, 98%, 98.5% or higher.

7. The solid dispersion of claim 1, wherein the solid dispersion is held at 40° C. and 75% RH for 6 months, and the purity of the compound represented by formula I is not less than 93%, 93.5%, 94%, 94.5%, 95%, 95.5%, 96%, 96.5%, 97%, 97.5%, 98%, 98.5% or higher.

8. A pharmaceutical composition comprising the solid dispersion of claim 1, and one or more pharmaceutically acceptable excipients.

9. The pharmaceutical composition of claim 8, wherein the content of the compound represented by formula I is 0.1 mg-1000 mg;
or, the content of the compound represented by formula I is 0.01%-50% based on the total weight of the pharmaceutical composition.

10. The pharmaceutical composition of claim 8, wherein it satisfies one or more of the following conditions:
(a) the pharmaceutical composition further comprises a filler, wherein the filler comprises one or more of microcrystalline cellulose, calcium hydrogen phosphate, mannitol, pregelatinized starch, and lactose; the content of the filler is 5%-90% based on the total weight of the pharmaceutical composition;
(b) the pharmaceutical composition further comprises a disintegrating agent, wherein the disintegrating agent comprises one or more of croscarmellose sodium, starch, sodium carboxymethyl starch and crospovidone; the content of the disintegrating agent is 1%-20% based on the total weight of the pharmaceutical composition;
(c) the pharmaceutical composition further comprises a lubricant, wherein the lubricant comprises one or more of magnesium stearate, zinc stearate, glyceryl behenate, sodium lauryl sulfate, hydrogenated vegetable oil, micronized silica, talc, and silica; the content of the lubricant is 0.5%-5% based on the total weight of the pharmaceutical composition.

11. A method for preparing the solid dispersion as defined in claim 1, comprising a method (1) which comprises a step of mixing the compound represented by formula I with the polyvinylpyrrolidone and an optional excipient in a melt extrusion device, and a step of heating and mixing the mixture and finally extruding a solid dispersion product; or a method (2) which comprises a step of mixing the compound represented by formula I with the polyvinylpyrrolidone and a solvent, and a step of removing the solvent; wherein the weight ratio of the compound represented by formula I to the polyvinylpyrrolidone is 1:3 to 1:7, and the proportion of polyvinylpyrrolidone is greater than 70% based on the total weight of the solid dispersion.

12. The method of claim 11, wherein the step for removing the solvent comprises one or more of rotary evaporation, spray drying, lyophilization, and film evaporation.

13. A method for preparing a pharmaceutical composition, comprising a step of preparing the solid dispersion of claim 1, and a step of mixing the solid dispersion with one or more pharmaceutically acceptable excipients.

14. A method for treating cancer comprising administering to a patient in need thereof an effective amount of the solid dispersion of claim 1 wherein the cancer comprises breast cancer, ovarian cancer, pancreatic cancer, prostate cancer, liver cancer or colon cancer.

15. A method for treating cancer comprising administering to a patient in need thereof an effective amount of the pharmaceutical composition of claim 8 wherein the cancer comprises breast cancer, ovarian cancer, pancreatic cancer, prostate cancer, liver cancer or colon cancer.

16. A method for treating cancer comprising administering to a patient in need thereof an effective amount of the pharmaceutical composition of claim 10 wherein the cancer comprises breast cancer, ovarian cancer, pancreatic cancer, prostate cancer, liver cancer or colon cancer.

* * * * *